United States Patent [19]

Lind

[11] Patent Number: 5,935,802
[45] Date of Patent: Aug. 10, 1999

[54] METHOD OF ASSAYING A BLOOD SAMPLE FOR PROTHROMBIN

[75] Inventor: Stuart E. Lind, Winnetka, Ill.

[73] Assignee: Evanston Northwestern Healthcare Research Institute, Evanston, Ill.

[21] Appl. No.: 09/132,091

[22] Filed: Aug. 10, 1998

[51] Int. Cl.$^6$ ..................................................... C12Q 1/56
[52] U.S. Cl. ............................................. 435/13; 435/214
[58] Field of Search .............................. 435/7.4, 13, 212, 435/214, 219

[56] References Cited

U.S. PATENT DOCUMENTS

| | | | |
|---|---|---|---|
| 4,769,320 | 9/1988 | Furie et al. | 435/7 |
| 5,252,712 | 10/1993 | Furie et al. | 530/389.3 |
| 5,453,370 | 9/1995 | Triplett et al. | 435/214 |
| 5,705,198 | 1/1998 | Triplett et al. | 424/542 |

FOREIGN PATENT DOCUMENTS

| | | | |
|---|---|---|---|
| 063698 | 3/1992 | Japan . | |
| 10-70979 | of 1998 | Japan . | |
| WO 96/27660 | 12/1996 | WIPO | C12N 9/74 |

OTHER PUBLICATIONS

Yamada et al., "Isolation and characterization of carinactivase, a novel prothrombin activator in *Echis carinatus* venom with a unique catalytic mechanism," *The Journal of Biological Chemistry*, vol. 271, No. 9, pp. 5200–5207, (1996).

Triplett et al., *Procedures for the Coagulation Laboratory*, Educational Products Divison American Society of Clinical Pathologists, Chicago, pp. 34–37 (1981).

Yamada D., Isolation and Characterization of Carinactivase, J of Biological Chemistry 271(9)5200–5207, 1996.

Yamada D., Prothrombin and Factor X Activator Activities in the Vernoms of Viperidae Snakes, Toxicon 35(11)1581–1589, 1997.

Francis J., A Rapid and Simple Micromethod for the Specific Determination of Descarboxylated Prothrombin, Medical Lab Sciences vol. 45 69–73, 1988.

Rob J., A Rapid and Highly Sensitive Chromogenic Microplate Assay for Quaitification of Rat and Human Prothrombin, Anal Biochem 245 222–225, Feb. 1997.

*Primary Examiner*—Ralph Gitomer
*Attorney, Agent, or Firm*—Marshall, O'Toole, Gerstein, Murray & Borun

[57] ABSTRACT

An improved method of assaying undiluted whole blood or undiluted plasma for prothrombin is disclosed. The improved method utilizes carinactivase-1 and calcium ions, and eliminates the need for a prothrombin-deficient plasma as a reference plasma.

19 Claims, 1 Drawing Sheet

METHOD OF ASSAYING A BLOOD SAMPLE FOR PROTHROMBIN

FIELD OF THE INVENTION

The present invention relates to an improved method of assaying an undiluted whole blood sample, or an undiluted blood plasma sample, for prothrombin. More particularly, the present invention relates to a method of assaying an undiluted blood or plasma sample using a composition containing carinactivase-1 and calcium ions. The improved method eliminates the need for a prothrombin-deficient plasma as a reference plasma, and is a more rapid, accurate, and economical assay for prothrombin. The assay can be performed in a wet chemistry format or in a dry phase test strip format.

BACKGROUND OF THE INVENTION

Prothrombin is a vitamin K-dependent plasma protein involved in blood coagulation. Prothrombin has a molecular weight of about 72,000 and is a calcium-binding protein that undergoes a conformational transition in the presence of calcium. When activated, prothrombin undergoes proteolytic cleavage at two sites to yield a two-chain molecule linked by a disulfide bond. This new product is thrombin. Thrombin converts fibrinogen to fibrin to produce the initial visible manifestation of coagulation, the soluble fibrin clot.

The proteolytic activation of prothrombin to form thrombin is a critical step in normal hemostasis. Prothrombin is synthesized in the liver where a prothrombin precursor undergoes posttranslational modification to yield the normal, functional form of prothrombin, which is known as "native prothrombin" and contains γ-carboxyglutamic acid. A nonfunctional, deficient form of prothrombin is known as descarboxyprothrombin, and is not activated to form thrombin.

In the presence of vitamin K antagonists, such as sodium warfarin (also known as COUMADIN®), or in the absence of vitamin K, prothrombin activity in the blood can be significantly diminished. Severe liver disease also can be associated with low plasma prothrombin activity. Thus, impaired synthesis of proteins (liver disease), inadequate supplies of vitamin K (vitamin K deficiency), or drugs that inhibit the action of vitamin K (sodium warfarin) lead to diminished plasma prothrombin activity in humans and other mammals.

COUMADIN® is used as an oral anticoagulant in the therapy or prevention of thrombotic disease. COUMADIN® lowers the activity of vitamin K-dependent blood coagulation proteins such as prothrombin. The appropriate COUMADIN® dose is established by monitoring the prothrombin time, or a one-stage coagulation assay. The appropriate dose also can be monitored by direct measurement of prothrombin coagulant activity using prothrombin deficient substrate plasma, but this is not a common procedure.

The prothrombin time, however, is a test influenced by blood level concentrations of two additional proteins, specifically, Factor X and Factor VII. An alternate method that is not in widespread use is to measure the level of prothrombin in the blood.

Direct assays for prothrombin coagulant activity are carried out by mixing test plasma with varying amounts of prothrombin-deficient plasma, followed by clotting and comparison with a standard curve. Echis carinatus assays using snake venom are used to measure total prothrombin, i.e., the sum of native prothrombin and descarboxyprothrombin. For individuals undergoing therapy using sodium warfarin, descarboxyprothrombin is present in the plasma, together with native prothrombin. The above-described assay for total prothrombin cannot differentiate between native prothrombin and descarboxyprothrombin, and, therefore, cannot be used to measure native prothrombin concentration in individuals undergoing sodium warfarin therapy.

Yamada et al., *J. Biol. Chem.*, 271(9), pp. 5200–5207 (1996), discloses the characterization of carinactivase-1 (CA-1), a prothrombin activator present in the venom of certain subspecies of Echis carinatus. This publication disclosed that CA-1 can be used to assay the plasma of individuals using a vitamin K antagonist, e.g., an oral anticoagulant. The disclosed assay requires mixing the test plasma with varying amounts of prothrombin-deficient plasma.

The current method of measuring plasma prothrombin levels requires making several dilutions of the plasma of interest, or a reference plasma, then mixing these diluted plasmas with a plasma deficient in prothrombin. Next, the prothrombin time of the mixtures is determined, and the prothrombin concentration of the plasma of interest is calculated from a standard curve established by assaying the reference plasma. Such assays typically are performed by specially trained laboratory technicians using coagulation machines. The current assay method for prothrombin, therefore, is labor intensive, expensive, and susceptible to inaccurate results due to technician error resulting from numerous manipulative steps.

It would be advantageous, therefore, to provide a method of determining plasma prothrombin concentration within minutes after adding a reagent to undiluted plasma or whole blood, without dilution or other special preparation of the sample, and without the use of prothrombin-deficient plasma. Such a method would be useful in monitoring prothrombin levels in individuals taking oral anticoagulants, suffering from liver disease, or whose prothrombin levels are measured for other clinical purposes.

Therefore, for an individual to monitor anticoagulant therapy, or to monitor a treatment to overcome a specific blood factor deficiency, an accurate and sensitive assay of undiluted whole blood and blood plasma for prothrombin is needed. The assay should permit the rapid detection and measurement of prothrombin in the test sample such that a correct medical treatment is implemented, monitored, and maintained. In addition, it would be advantageous for the assay method to utilize a dry phase test strip for the easy and economical determination of prothrombin in undiluted whole blood or plasma.

Furthermore, any method of assaying for prothrombin in whole blood or plasma should yield accurate, trustworthy, and reproducible results by utilizing a composition that undergoes a detectable transition as a result of an interaction with normal prothrombin, and not as a result of a competing interaction with a deficient form of prothrombin, i.e., descarboxyprothrombin. Moreover, it would be advantageous if the assay method for prothrombin is suitable for use in dry phase reagent test strips for the rapid, economical, and accurate determination of prothrombin in whole blood or plasma.

Therefore, in order to monitor the course of medical treatment for anticoagulants to determine the effectiveness of the treatment, or to overcome a specific blood factor deficiency, simple, accurate, and inexpensive detection assays for prothrombin are needed. Furthermore, the assay method should obviate dilution of the test sample and the use of prothrombin-deficient plasma.

Present-day assays for prothrombin do not assay undiluted blood or plasma, and have the disadvantages of requiring the use of prothrombin-deficient plasma. Surprisingly and unexpectedly, the composition and method of the present invention provide a composition that can be used in the assay of undiluted whole blood or plasma for prothrombin, without the use of a prothrombin-deficient plasma. By providing an accurate method of determining the concentration of prothrombin in a test sample, in an easy to use format, such as a dip-and-read test strip, the assay can be performed by laboratory personnel, or at home, to afford immediate and trustworthy test results. In addition, a test strip method can be performed to more precisely monitor the level of prothrombin in undiluted whole blood or plasma and/or the success of the medical treatment the individual is undergoing.

SUMMARY OF THE INVENTION

The present invention is directed to an improved method and device for assaying an undiluted whole blood or plasma sample for prothrombin. In particular, the present invention is directed to an assay of undiluted whole blood or plasma using a composition containing carinactivase-1 and calcium ions, wherein the need to use a prothrombin-deficient plasma as a reference plasma is eliminated. The assay can be performed by wet chemistry methods or by a dry chemistry test strip format.

Therefore, one aspect of the present invention is to provide a method of assaying an undiluted whole blood or plasma sample for prothrombin utilizing a venom fraction containing carinactivase-1, calcium ions, and an optional indicator capable of providing a detectable response to the presence or concentration of prothrombin in the test sample.

In accordance with an important feature of the present invention, a more accurate and reliable assay for prothrombin is achieved because the test sample is not diluted and the use of prothrombindeficient plasma is eliminated. Accordingly, manipulative errors that can reduce the accuracy of assay results are avoided.

Therefore, one aspect of the present invention to provide a new and improved method and test device for determining the concentration of native prothrombin in a liquid test sample.

Another aspect of the present invention is to provide a simple, trustworthy, accurate, and reproducible method of assaying undiluted whole blood or blood plasma, for prothrombin.

Another aspect of the present invention is to provide a method of assaying undiluted whole blood, or blood plasma, for prothrombin utilizing a composition comprising: (a) carinactivase-1, (b) calcium ions, and (c) an optional indicator.

Another aspect of the present invention is to provide a new and improved test device for detection of prothrombin in a test sample to produce a visible change, such as a change in color, of the test device, indicative of the concentration of the native prothrombin in the test sample.

Yet another aspect of the present invention is to provide a method of assaying for prothrombin concentration, which can be correlated to (a) a vitamin K deficiency or various forms of liver disease, including hepatocellular carcinoma, or (b) monitoring anticoagulant therapy with sodium warfin, or (c) monitoring treatments for specific blood factor deficiencies, i.e., treating of a Factor II deficiency.

These and other aspects and advantages of the present invention will become apparent from the following detailed description of the preferred embodiments.

DETAILED DESCRIPTION OF THE PREFERRED EMBODIMENTS

Figure 1:
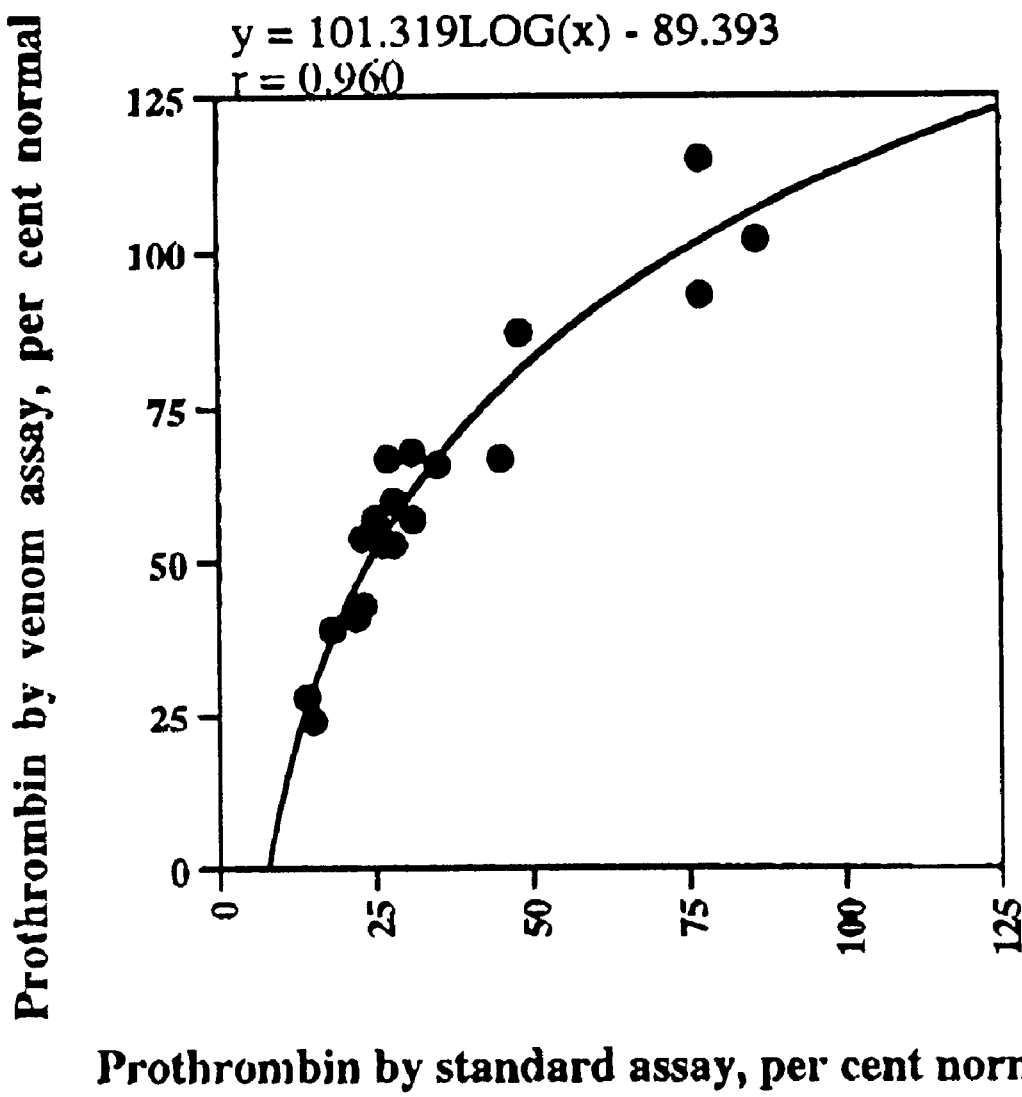
FIG. 1 is a plot comparing the present venom assay method for prothrombin to a standard assay method for prothrombin using plasmas obtained from patients administered warfarin sodium.

In accordance with the method of the present invention, an assay for native prothrombin in undiluted whole blood or undiluted blood plasma is accomplished by utilizing a reagent composition comprising: (a) carinactivase-1, (b) calcium ions, (c) an optional indicator, and (d) a buffer to provide a pH of about 6 to about 8.

Prior assays for prothrombin relied upon dilutions of the test sample, and upon the use of prothrombin-deficient plasma to obtain a prothrombin time. These prior assay methods are tedious, slow, and can result in inaccurate assays because the numerous manipulative tests can lead to technician error. The present method of assaying for prothrombin eliminates the need for sample dilution, but rather utilizes undiluted whole blood or undiluted plasma. In addition, the prothrombin assay does not rely upon a prothrombin-deficient plasma.

The present method utilizes carinactivase-1 and calcium ions to determine the prothrombin concentration of an undiluted test sample. Assay results can be measured in terms of coagulation time, hydrolysis of a chromogenic or fluorogenic substrate leading to a detectable response, or a chromogenic indicator capable of undergoing a color transition that can be correlated to prothrombin concentration.

The term "detectable response" as used herein means a chemical or physical change that is capable of being perceived, either visually or instrumentally. The magnitude of the detectable response is proportional to the presence and concentration of a specific analyte, e.g., native prothrombin, in an aqueous test sample. Nonlimiting examples of detectable responses include a change in, or an occurrence of, color, fluorescence, reflectance, pH, chemilumnimescence, spectrophotometry, or colorimetry.

The present method can be performed by untrained individuals, in the home, to monitor oral anticoagulant therapy, or to monitor the progression of a disease, for example. The method provides fast and reliable assays for prothrombin, typically in about one to about three minutes.

In accordance with an important feature of the present invention, the reagent composition used in the method contains carinactivase-1. Carinactivase-1 is present in the reagent composition in an amount sufficient to discriminate between prothrombin levels in the plasma of individuals undergoing warfarin treatment, wherein the prothrombin concentration is determined by a standard present day assay. Typically, the CA-1 is present in an amount of about 10 nM to about 1 mM, and preferably about 0.001 to about 0.1 mM. To achieve the full advantages of the present invention, the reagent composition contains about 0.01 to about 0.1 mM of carinactivase-1.

Carinactivase-1 is a component of the venom of the viper *Echis carinatus*. The venom also contains ecarin, and it is necessary to separate the carinactivase-1 from the ecarin before using the carinactivase-1 in the reagent composition.

The present method assays for native prothrombin, and utilizes carinactivase-1 that is free of ecarin. Ecarin is capable of interacting with both native prothrombin and descarboxyprothrombin. Accordingly, the ecarin is removed from the venom to avoid a competing interaction that can lead to inaccurate assay results. One method of isolating carinactivase-1 from *Echis carinatus* venom is disclosed in D. Yamada et al., *J. Biol. Chem.*, 271(9), 5200–5207 (1996), incorporated herein by reference.

Carinactivase-1 is potent prothrombin activator in the presence of calcium ions. However, carinactivase-1 is inactive when calcium ions are absent. Therefore, the reagent composition contains about 1 to about 30 mM, and preferably about 2 to about 20 mM, calcium ions. To achieve the full advantage of the present invention, the reagent composition contains about 3 to about 15 mM calcium ions.

The source of the calcium ions can be any calcium salt having a sufficient water solubility to provide about 1 to about 30 mM calcium ions. The anion can be organic or inorganic in structure. Examples of such salts include, but are not limited to, calcium chloride, calcium nitrate, calcium acetate, calcium carbonate, calcium bromide, calcium tartrate, calcium iodide, calcium oxalate, and mixtures thereof.

The reagent composition is buffered to a pH of about 6 to about 8, and preferably about 7 to about 8. To achieve the full advantage of the present invention, the composition is buffered to a pH of about 7.2 to about 7.8.

A buffer typically is included in the reagent composition at a concentration of about 100 mM and about 600 mM, although in particular situations, the concentration of the buffer can be above or below this range.

A reagent composition invention is buffered to a suitable pH with a buffer such as acetate; BICINE; phthalate; borate; trichloracetate; sulfosalicylate; phosphate; tartarate; citrate; succinate; maleic acid; 2,2-bis(hydroxymethyl)-2,2',2"-nitrilo-triethanol; 3,3-dimethylglutaric acid; 3-N-morpholino-propanesulfonic acid (MOPS); malonic acid; 1,3-bis[tris(hydroxymethyl)methylamino]propane (Bis-TRIS); tris(hydroxymethyl)aminomethane (TRIS); tris(hydroxy-methyl)aminomethanemaleic acid (TRIS-maleate); tris-(hydroxymethyl)aminomethanemalonic acid (TRIS-malonate); 3-N-(trishydroxymethyl)methylamino-2-hydroxy-propane sulfonic acid (TAPSO); 2-([tris(hydroxymethyl)methyl]amino)ethanesulfonic acid (TES); 1,4-piperazinebis(ethanesulfonic acid) (PIPES); 4-morpholinoethanesulfonic acid (MES); N-2-hydroxyethylpiperazine-N'-2-ethanesulfonic acid (HEPES); and other suitable buffers that are well known in the art, or mixtures thereof.

The reagent composition containing carinactivase-1, calcium ions, and a buffer activates prothrombin. Therefore, when the reagent composition is added to a test sample, the concentration of prothrombin in the test sample can be determined from a detectable response attributable to prothrombin activation, and correlation of the detectable response to response of standardized samples containing known amounts of prothrombin. The detectable response can be measurement of coagulation time, or can be a chromogenic or fluorogenic response.

In the case of a chromogenic or fluorogenic response, the reagent composition then also includes about 0.1 to about 5 mM, and preferably about 0.2 to about 3 mM, of an indicator. To achieve the full advantage of the present invention, the reagent composition contains about 0.3 to about 2 mM of an indicator.

The indicator can be any compound that undergoes a detectable response as a result of the interaction between carinactivase-1/calcium ions and prothrombin. Preferred indicators undergo a color transition in response to the interaction, wherein the intensity and degree of the color transition can be correlated to the concentration of prothrombin in the test sample.

Examples of indicators include, but are not limited to, peptidylarginine p-nitroanilide or peptidyl-7-amido-4-methylcoumarin substrates, such as D-phenylalanyl-L-pipecolyl-L-arginyl-p-nitroanilide, N-p-tosyl-glycyl-L-prolyl-L-arginyl-7-amido-4-methylcoumarin.

Other optional ingredients, in addition to the indicator, that do not materially alter the nature or the function of the essential ingredients, and that do not interfere with the assay for prothrombin, also can be included in the reagent composition. For example, the reagent composition optionally can include a compound to improve wetting of a test pad of a drug test device by the test sample. This compound usually is an anionic surfactant or a nonionic surfactant. An anionic surfactant, such as a long carbon chain sulfate or sulfonate, like sodium dodecyl sulfate, dioctyl sodium sulfosuccinate, and sodium dodecylbenzene sulphonate, can be used. Nonionic surfactants, such as an octoxynyol, a nonoxynol, or an ethoxylated fatty alcohol, also can be included in the reagent composition. The surfactant is included in the reagent composition in a concentration of 0 to about 200 mM, and preferably in a concentration of about 50 to about 200 mM.

The reagent composition also can include a polymeric material that improves the stability and uniformity of the color transition of the test device. Suitable polymeric materials include, but are not limited to, polyvinylpyrrolidone, polyvinyl alcohol, gum arabic, gelatin, algin, carrageenan, casein, albumin, methyl cellulose, and similar natural and synthetic polymeric materials. The polymeric material generally is included in the reagent composition in an amount of 0% to about 5%, and preferably about 1% to about 4%, by total weight of the reagent composition.

In addition, to improve the color resolution and differentiation of the color transition in a chromogenic assay, inert background dyes can be included in the reagent composition. Suitable background dyes include, but are not limited to, ethyl orange (4-(4-diethylaminophenylazo)benzenesulfonic acid); Orange G (4-(2-hydroxy-(7,9 sodium disulfonate)-1-naphthylazo)benzene); disperse orange 11, 13, or 25; calcomine orange; methyl orange; and orange II (4-(2-hydroxy-1-naphthylazo)benzenesulfonic acid), or combinations thereof. A background dye is included in the reagent composition of the present invention in a concentration of 0 to about 2 mM, and preferably about 0.1 to about 1 mM.

The carrier vehicle for the ingredients included in the reagent composition includes water. However, organic solvents such as methanol, ethanol, isopropyl alcohol, ethylene glycol, propylene glycol, acetone, dimethylformamide, dimethylsulfoxide, aceto-nitrile, ethyl acetate, and similar solvents can be included in the carrier vehicle. The selection of a suitable organic solvent or solvents, in addition to water, to include in the carrier vehicle of the indicator reagent composition is within the capability of those skilled in the art of designing diagnostic assays.

The amount of organic solvent present in the reagent composition generally is 0% to about 90%, and preferably about 10% to about 70%, by weight of the carrier vehicle. A carrier solvent comprising water and an organic solvent, like methanol or ethanol, is especially preferred because a carrier matrix impregnated with the reagent composition can be dried within a few to several minutes.

As previously described, the reagent composition undergoes a detectable response upon contact with an undiluted test sample to demonstrate the presence and concentration of prothrombin in the test sample. The detectable response can be in the form of a measurement, like the coagulation time. Alternatively, the detectable response can be in the form of a light emissions or a color transition. The intensity and degree of the color transition can be used to quantitatively determine the concentration of prothrombin in the test sample. Selection of the proper indicator provides a sufficiently resolved and differentiated color transition such that the amount of prothrombin in a test sample can be measured and accurately determined without the use of color-measuring instruments, such as spectrophotometers or calorimeters. However, if desired, such color-measuring instruments can be used to measure the difference in color degree and intensity between the test sample and a solution having a known concentration of prothrombin.

Accordingly, an assay that utilizes a reagent composition of the present invention improves the accuracy and reliability of the assay and also increases confidence in the assay. Additionally, because the assay is performed without the need to dilute the test sample, and without the use of a prothrombin-deficient plasma, the assay can be performed at home by an untrained individual, as opposed to trained physicians or technicians in the laboratory.

As discussed above, prior methods of assaying for prothrombin required multiple dilutions of the test sample, and the use of a prothrombindeficient plasma. In contrast, the present method is performed on undiluted whole blood or undiluted plasma, and does not rely upon prothrombin-deficient plasma.

The present method of assaying for prothrombin can be performed as a wet method or as a dry phase test-strip method. In the wet method, an undiluted whole blood or plasma sample, e.g., about 10 to about 100 µL is added to a liquid reagent composition. The resulting mixture then is examined for a detectable response, e.g., coagulation time or a color transition, and the detectable response is correlated to the prothrombin concentration of the test sample.

Alternatively, an undiluted test sample is allowed to contact a test pad. The test pad has a reagent composition incorporated therein, as described in detail hereafter. The test pad then is examined for a detectable response, and the response is correlated to the prothrombin concentration of the test sample.

To illustrate the new and unexpected features of the present invention, the following indicator reagent composition was prepared. The indicator reagent composition contained:

Carinactivase-1—0.01 mM
Calcium ions[1]—6.25 mM
Buffer[2] (pH 7.4)—10 mM
Water—q.s.

1) calcium ions added as calcium chloride; and
2) buffer was 10 mM TRIS hydrochloride (TRIS-HCl) and 150 mM sodium chloride.

The carinactivase-1 used in the reagent composition was obtained by passing a solution of lyophilized venom form *Echis carinatus* dissolved in 50 mM TRIS-HCl (pH 8.0) over a Blue Sepharose column in 50 mM TRIS-HCl (pH 8.0). The fractions containing CA-1 were identified by clotting normal plasma. The fractions containing CA-1 were pooled and diluted in a buffered solution (pH 7.4) containing calcium chloride (150 mM).

The reagent composition described above was used to assay undiluted test samples of plasma taken from individuals administered warfarin sodium for prothrombin. The assay results were compared to assay results for prothrombin obtained by the standard prior art method for measuring plasma prothrombin levels.

The assays on undiluted test samples for prothrombin using the above reagent composition were performed by adding 0.1 ml of undiluted plasma to 0.1 ml of the reagent composition and measuring the time required for the resulting mixture to clot. The native prothrombin concentration then was determined by reference to a standard curve of clotting time vs. prothrombin concentration.

The prior art assay for prothrombin was performed on a different portion of the same test samples by a standard method. The test plasma was diluted in prothrombin-deficient plasma and the clotting time was determined after the addition of a solution containing tissue thromboplastin and calcium ions. The prothrombin level was calculated by comparing the clotting time to a standard curve of clotting time vs. prothrombin concentration. This method is disclosed in D. A. Triplett et al., *American Society of Clinical Pathologists*, (1981), pages 34–37, incorporated herein by reference.

The plot in FIG. 1 shows that prothrombin assays performed by the present method correlate well with prothrombin assays performed by the standard, prior art method. The present method offers the advantage of a more rapid assay that can be conducted by untrained personnel at home, with a reduced possibility of operation error and at a reduced cost. These advantages are attributed to the fact that the present assay method eliminates dilution of the test sample, and eliminates the use of prothrombin-deficient plasma, which is a reagent that is short supply.

To further demonstrate the new and unexpected results achieved by the method of the present invention, a reagent composition can be in a dry phase test strip assay for prothrombin. The dry phase test strip assay utilizing the reagent composition of the present invention is performed in accordance with methods well known in the art. In general, the assay for prothrombin is performed by contacting the undiluted whole blood or plasma with an analyte detection device that includes the reagent composition. The analyte detection device can be dipped into the test sample, or the test sample can be applied to the analyte detection device dropwise. In the case of undiluted whole blood, the highly colored cellular material can be wiped or blotted from the analyte detection device before examining the detection device for a response. In one embodiment, the resulting change in color of the analyte detection device demonstrates the presence of prothrombin; and, if so designed, the resulting color transition can be compared to a standardized color chart to provide a quantitative measurement of the concentration of prothrombin in the undiluted whole blood or plasma.

Typically, the analyte detection device is a reagent-impregnated test strip, designed either as a single pad test strip (to assay only for a single analyte) or as a multiple pad test strip (to assay for several analytes simultaneously). For either type of reagent-impregnated test strip, the test strip includes a support strip, or handle, normally constructed from a hydrophobic plastic, and a reagent test pad, comprising a bibulous or a nonbibulous carrier matrix incorporating the reagent composition. In general, the carrier matrix is an absorbent material that allows the test sample to move in response to capillary forces through the carrier matrix to contact the reagent composition and produce a detectable response, like a measurable color transition. In the assay of an undiluted whole blood sample, the carrier matrix generally is not permeable to the cellular material. Therefore, the highly colored cells can be wiped or blotted from the test pad and not interfere with or mask the assay for prothrombin. Furthermore, if the carrier matrix is permeable to the cellular material, persons of ordinary skill in the art are aware of techniques and devices to separate the cellular material from the test sample to eliminate the interfering effects of the cellular material.

The carrier matrix can be any substance capable of incorporating the chemical reagents required to perform the assay of interest, as long as the carrier matrix is substantially inert with respect to the chemical reagents, and is porous or absorbent relative to the soluble components of the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth, and the like; argillaceous substances, cloth, hydrophilic natural polymeric materials, particularly cellulose material, like cellulosic beads, and especially fiber-containing papers such as filter paper or chromatographic paper, synthetic or modified naturally occurring polymers, such as crosslinked gelatin, cellulose acetate, polyvinyl chloride, polyacrylamide, cellulose, polyvinyl alcohol, polysulfones, polyesters, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix comprises a hydrophilic or absorptive material. The carrier matrix is most advantageously constructed from bibulous filter paper or nonbibulous polymeric films. The handle usually is formed from a hydrophobic material such as cellulose acetate, polyethylene terephthalate, polycarbonate, or polystyrene.

If the test strip is designed to assay for prothrombin in a test sample, the carrier matrix can be any bibulous or nonbibulous material that allows permeation by the soluble components of the test sample to saturate the test pad of the test strip that is impregnated with the reagent composition. A preferred carrier matrix is a hydrophilic, bibulous matrix, including cellulosic materials, such as paper, and preferably filter paper. To achieve the full advantage of the present invention, in the assay for prothrombin in a test sample, the carrier matrix is a hydrophilic, nonbibulous matrix, including polymeric films, such as a polyurethane or a crosslinked gelatin. Such polymeric films possess all of the qualities required of a carrier matrix of the present invention, including suspending and positioning both the essential ingredients and any optional ingredients included in the reagent composition, and permeability of the soluble components of the test sample through the carrier matrix.

To achieve the full advantage of the present invention, the reagent composition is impregnated into a suitable carrier matrix and utilized in a dry phase test strip for the assay of prothrombin in a test sample. The method of the present invention affords an economical, accurate, and reliable assay that can be performed at home or in the laboratory for the presence or concentration of prothrombin in an undiluted test sample. In addition, the method of the present invention allows detection, differentiation and measurement of a low concentration of prothrombin in the test sample therefore making the assay more useful clinically.

A dry phase test strip assay useful for a prothrombin assay is prepared by first forming an aqueous or an aqueous alcohol solution including about 0.1 mM to about 5 mM of an indicator, such as a nitroanilide or a methylcoumarin substrate, about 0.001 mM to about 1 mM of carinactivase-1, about 1 to about 30 mM calcium ions, about 100 to about 600 mm buffer, and any other desired optional ingredients, or solvents. A nonbibulous matrix, such as a polyurethane film, or a bibulous matrix, such as filter paper, then is saturated or impregnated with the solution by immersing or by spraying the solution onto sheets or precut strips or pads of the polyurethane film or filter paper.

Then, after removing the aqueous or aqueous alcohol solvent by drying in a forced air oven at a temperature of from about 30° C. to about 100° C. for about 2 minutes to about 5 minutes, the saturated or impregnated polyurethane film or filter paper, if necessary, is cut to an appropriate size, such as a pad having dimensions from about 0.2 in. (inch) (0.5 cm) by about 0.5 in. (1.3 cm) to about 0.5 in. (1.3 cm) by about 1 in. (2.5 cm).

It should be understood that it is well within the experimental techniques of those skilled in the art of preparing test devices to determine the proper balance between size of reagent pad, the strength of indicator reagent compositions solutions, the amount of test sample, and the method of introducing the test sample to the test strip, such as by pipetting rather than dipping, in order to design a quantitative assay for prothrombin utilizing the method and composition of the present invention.

The dried, twice-impregnated polyurethane film or filter paper then is secured to an opaque or transparent hydrophobic plastic handle with double-sided adhesive tape. The resulting test strip then is contacted with an undiluted whole blood or an undiluted blood plasma sample for a sufficient time to saturate the test pad with the sample. After waiting a predetermined time, such as from about 0.5 minutes to about 10 minutes, the test strip is examined, either visually or by instrument, for a response. If necessary, the cellular material present in the test sample is wiped or blotted from the test strip before examining the test strip for a response. The detectable response, such as a color transition, if any, of the test pad reveals the presence or concentration of prothrombin in the test sample.

In many cases, simple visual observation of the test strip provides the desired information. If more accurate information is required, a standardized color chart bearing color spots corresponding to various known concentrations can be prepared for the particular reagent composition used in the test strip. The resulting color of the test strip after contact with the test sample then can be compared with the color spots on the chart to determine the concentration of prothrombin in the test sample. If a still more accurate determination is required, a spectrophotometer or calorimeter can be used to more precisely determine the degree of color transition. In addition, the dry phase test strip assay can be made quantitative by employing spectrophotometric or calorimetric techniques, as opposed to visual techniques, in order to more reliably and more accurately measure the degree of color transition, and, therefore, more accurately measure the concentration of prothrombin in the test sample.

In accordance with an important feature of the present invention, the continuing and substantial problems associated with a native prothrombin assay are eliminated. These problems include dilution of the test sample, which is a source for operator error, and the use of a prothrombin-deficient plasma. The present method also can be practiced by untrained individuals in the home. Therefore, the present method is faster, more accurate, and less costly than standard prothrombin assays.

A test pad incorporating a reagent composition of the present invention can be included in a multideterminant test strip to assay for prothrombin. If an individual is testing undiluted whole blood for prothrombin to monitor the course of oral anticoagulant therapy, the individual also could test for other blood constituents, like glucose, potassium, or occult blood, for example. Accordingly, the individual does not require separate test kits to perform separate assays, and a single, small blood sample can be used for all assays.

The wet phase and dry phase test strip assays of the present invention for prothrombin are most useful for assays performed at home, in private physician laboratories, and in emergency rooms. For example, the dry phase test strip assay for prothrombin in whole blood could replace the current INR assay technique in the assay for prothrombin.

Obviously, many modifications and variations of the invention as hereinbefore set forth can be made without departing from the spirit and scope thereof, and, therefore, only such limitations should be imposed as are indicated by the appended claims.

What is claimed is:

1. A method of assaying an undiluted whole blood or undiluted blood plasma sample for native prothrombin comprising:
  (a) contacting the sample with a reagent composition which forms a detectable response, said reagent composition comprising:
    (i) about 10 nM to about 0.1 mM of carinactivase-1,
    (ii) about 1 to about 30 mM calcium ions,
    (iii) about 10 to about 600 mM of a buffer to provide a pH of about 7 to about 8; and
    (iv) about 0.1 to about 5 mM of an indicator;
  (b) measuring an intensity of the detectable response; and
  (c) correlating the intensity of the detectable response to a prothrombin concentration of the sample,
  wherein the carinactivase-1 is free of ecarin and the reagent composition interacts with native prothrombin and is inert with respect to descarboxyprothrobin.

2. The method of claim 1 wherein the reagent composition comprises about 0.001 to about 0.1 mM of carinactivase-1.

3. The method of claim 1 wherein the carinactivase-1 is isolated from the venom of Echis carinatus.

4. The method of claim 1 wherein the reagent composition comprises about 2 to about 20 mM calcium ions.

5. The method of claim 1 wherein the reagent composition is buffered to a pH of about 7.2 to about 7.8.

6. The method of claim 1 wherein the reagent composition comprises about 0.2 to about 3 mM of an indicator.

7. The method of claim 1 wherein the indicator comprises a peptidylarginie-p-nitro-anilide substrate or a peptidyl-7-amido-4-methylcoumarin substrate.

8. The method of claim 1 wherein the detectable response is a change in color, fluorescence, reflectance, pH, chemoluminescence, spectrophotometry, or colorimetry.

9. The method of claim 1 wherein the detectable response is measured visually or instrumentally.

10. The method of claim 1 wherein the detectable response is measured in the absence of prothrombin-deficient plasma.

11. The method of claim 1 wherein the reagent composition further comprises 0 to 200 mM of a surfactant and 0 to 5% by weight of a polymeric material.

12. A method of assaying an undiluted whole blood or undiluted blood plasma sample for prothrombin comprising:
  (a) contacting the sample or the undiluted blood plasma with a reagent composition comprising:
    (i) about 10 nm to about 0.1 mM of carinactivase-1,
    (ii) about 1 to about 30 mM calcium ions,
    (iii) about 100 mM to about 600 mM of a buffer to provide a pH of about 7 to about 8, wherein the carinactivase-1 is free of ecarin and the reagent composition interacts with native prothrombin and is inert with respect to descarboxprothrombin; and
  (b) measuring a clotting time of the sample; and
  (c) correlating the clotting time to a prothrombin concentration of the sample.

13. The method of claim 12 wherein the clotting time is determined in the absence of prothrombin-deficient plasma.

14. The method of claim 12 wherein the prothrombin concentration is correlated to a vitamin K deficiency, a liver disease, a Factor II blood deficiency, or anticoagulant therapy with sodium warfarin.

15. A test strip for assaying an undiluted whole blood sample or an undiluted blood plasma sample for native prothrombin comprising:
  (a) a support strip, and
  (b) a test pad secured to the support strip, said test pad comprising:
    (i) a carrier matrix, and
    (ii) a reagent composition incorporated into the carrier matrix, said composition comprising:
      (A) about 10 nM to about 0.1 mM of carinactivase-1, wherein the carinactivase-1 is free of ecarin,
      (B) about 1 to about 30 mM calcium ions,
      (C) about 100 mM to about 600 mM of a buffer to provide a pH of about 7 to about 8; and
      (D) about 0.1 to about 5 mM of an indicator,
    wherein the reagent composition intracts with native prothrombin and is inert with respect to descarboxyprothrombin.

16. A method of assaying for native prothrombin concentration comprising:
  (a) contacting a test strip of claim 15 with an undiluted whole blood sample or an undiluted plasma sample,
  (b) examining the test strip for a detectable response, and
  (c) correlating the detectable response to the native prothrombin concentration.

17. The method of claim 16 wherein the detectable response is correlated to clotting of the sample.

18. The method of claim 16 wherein the detectable response is a change in color, fluorescence, reflectance, pH, chemiluminescence, spectrophotometry, or colorimetry.

19. A method of assaying for a native prothrombin concentration of undiluted whole blood or undiluted plasma comprising:
  (a) contacting the undiluted whole blood or undiluted plasma with an analyte detection device comprising a test pad containing a reagent composition comprising:
    (i) about 10 nM to about 0.1 mM of carinactivase-1,
    (ii) about 1 to about 30 mM calcium ions,
    (iii) about 100 mM to about 600 mM of a buffer to provide a pH of about 7 to about 8, and
    (iv) about 0.1 to about 5 mM of an indicator, wherein the carinactivase-1 is free of ecarin and the reagent, composition interacts with native prothrombin and is inert with respect to descarboxyprothrombin; and
  (b) examining the analyte detection device for a detectable response to the native prothrombin concentration of the undiluted whole blood or undiluted plasma.

* * * * *

UNITED STATES PATENT AND TRADEMARK OFFICE
CERTIFICATE OF CORRECTION

PATENT NO. : 5,935,802
DATED : August 10, 1999
INVENTOR(S) : Stuart E. Lind

It is certified that error appears in the above-identified patent and that said Letters Patent is hereby corrected as shown below:

Column 11, line 26, "(iii) about 10" should be --(iii) about 100 mM--

Column 11, line 63, "10 nm" should be --10 nM--

Signed and Sealed this

Twenty-sixth Day of September, 2000

Attest:

Q. TODD DICKINSON

*Attesting Officer*            *Director of Patents and Trademarks*